(12) United States Patent
Berzak et al.

(10) Patent No.: US 11,003,852 B2
(45) Date of Patent: May 11, 2021

(54) PREDICTING NATIVE LANGUAGE FROM GAZE

(71) Applicant: Massachusetts Institute of Technology, Cambridge, MA (US)

(72) Inventors: Yevgeni Berzak, Somerville, MA (US); Boris Katz, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 393 days.

(21) Appl. No.: 16/130,662

(22) Filed: Sep. 13, 2018

(65) Prior Publication Data

US 2019/0079917 A1    Mar. 14, 2019

Related U.S. Application Data

(60) Provisional application No. 62/558,710, filed on Sep. 14, 2017, provisional application No. 62/558,765, filed on Sep. 14, 2017.

(51) Int. Cl.
| | |
|---|---|
| *G06F 40/263* | (2020.01) |
| *G06F 3/01* | (2006.01) |
| *G06F 17/18* | (2006.01) |
| *G06K 9/00* | (2006.01) |
| *G06F 40/30* | (2020.01) |
| *G06N 3/08* | (2006.01) |
| *G06N 20/00* | (2019.01) |
| *G09B 5/02* | (2006.01) |

(Continued)

(52) U.S. Cl.
CPC .......... *G06F 40/263* (2020.01); *G06F 3/013* (2013.01); *G06F 17/18* (2013.01); *G06F 40/30* (2020.01); *G06K 9/0061* (2013.01); *G06K 9/00335* (2013.01); *G06K 9/00604* (2013.01); *G06K 9/00617* (2013.01); *G06N 3/08* (2013.01); *G06N 20/00* (2019.01); *G09B 5/02* (2013.01); *G09B 17/003* (2013.01); *G09B 19/06* (2013.01)

(58) Field of Classification Search
CPC ........ G06F 40/263; G06F 40/30; G06F 3/013; G06F 17/18; G06F 3/005; G06K 9/00604; G06K 9/0061; G06K 9/00617; G06K 9/00335; G09B 5/02; G09B 17/003; G09B 19/06; G06N 20/00; G06N 3/08; G16H 50/70; A61B 5/7267; A61B 5/163
USPC ........................................................... 704/3
See application file for complete search history.

(56) References Cited

U.S. PATENT DOCUMENTS

2019/0080623 A1    3/2019 Berzak

OTHER PUBLICATIONS

Rayner, K., "Eye Movements in Reading and Information Processing: 20 Years of Research", Psychological Bulletin, vol. 124, No. 3 (1998).

(Continued)

*Primary Examiner* — Thierry L Pham
(74) *Attorney, Agent, or Firm* — Hamilton, Brook, Smith & Reynolds, P.C.

(57) ABSTRACT

In an embodiment, a method includes presenting, on a display, sample text in a given language to a user. The method further includes recording eye fixation times for each word of the sample text for the user and recording saccade times between each pair of fixations of the sample text. The method further includes comparing features of the gaze pattern of the user to features of a gaze pattern of a plurality of training readers. Each training reader (e.g., training user) has a known native language. The method further generates a probability of at least one an estimated native language of the user based on the results of the comparison.

20 Claims, 6 Drawing Sheets

(51) Int. Cl.
G09B 17/00 (2006.01)
G09B 19/06 (2006.01)

(56) References Cited

OTHER PUBLICATIONS

Rayner, K., et al., "Psychology of Reading", 2nd Edition, Psychology Press (2012).
Berzak, Y., et al. "Predicting Native Language from Gaze", May 2, 2017.
Barrett, M., et al. "Reading behavior predicts syntactic categories", Proceedings of the 19th Conference Language Learning pp. 345-349, Beijing, China, Jul. 30-31, 2015.
Barrett, M., et al., "Using reading behavior to predict grammatical functions", Proceedings of the Sixth Workshop on Cognitive Aspects of Computational Language Learning, pp. 1-5, Lisbon, Portugal, Sep. 18, 2015.
Barrett, M., et al, "Weakly Supervised Part-of-Speech Tagging Using Eye-Tracking Data", Proceedings of the 54th Annual Meeting of the Association for Computational Linguistics, pp. 579-584, Berlin, Germany, Aug. 7-12, 2016.
Berzak, Y., et al, "Contrastive Analysis with Predictive Power: Typology Driven Estimation of Grammatical Error Distributions in ESL", 18th Conference on Computational Natural Language Learning, Mar. 24, 2016.
Berzak, Y., et al, "Reconstructing Native Language Typology from Foreign Language Usage", Center for Brains, Minds & Machines, May 28, 2014.
Brooke, J., et al., "Measuring Interlanguage: Native Language Identification with L1-influence Metrics", LREC, pp. 779-784, 2012.
Bykh, S., et al., "Advancing Linguistic Features and Insights by Label-informed Feature Grouping: An Exploration in the Context of Native Language Identification", Proceedings of COLING 2016, the 26th International Conference on Computational Linguistics: Technical Papers, pp. 739-749, Osaka, Japan, Dec. 11-17, 2016.
Byrd, R.H., et al., "A Limited Memory Algorithm for Bound Constrained Optimization", Northwestern University, Dept of Electrical Engineering and Computer Science, May 1994.
Collins, C., et al., "Syntatic Structures of the World Languages", SSWL:directory:about, downloaded from internet http://sswl.railsplayground.net/about; Oct. 19, 2018.
Cop, U., et al., "Eye Movement Patterns in Natural Reading: A Comparison of Monolingual and Bilingual Reading of a Novel", PLOS One, 10(8):1-38, Aug. 19, 2015.
Dussias, P., et al. "Uses of Eye-Tracking Data in Second Language Sentence Processing Research", Annual Review of Applied Linguistics, 30, pp. 149-166, (2010).
Jarvis, S., et al., "Crosslinguistic Influence in Language and Cognition", Sociolinguistic Studies, vol. 6.3, pp. 603-607, 2012.
Klerke, S., et al. "Improving Sentence Compression by Learning to Predict Gaze", Proceedings of NAACL-HLT, pp. 1528-1533, 2016.
Koppel, M., et al., "Determining an Author's Native Language by Mining a Text for Errors", KDD '05, Aug. 21-24, 2005.
Lewis, M.P., et al., "Ethnologue: Languages of Ecuador", Ethnologue, 18th Edition, 2015.
Littel, P., et al. "URIEL and long2vec: Representing languages as typological, geographical, and phylogenetic vectors", Proceedings of the 15th Conference of the European Chapter of the Association for Computational Linguisitcs: vol. 2, pp. 8-14, Valencia, Spain, Apr. 3-7, 2017.
Malmasi, S., et al., "Language Transfer Hypotheses with Linear SVM Weights", EMNLP, pp. 1385-1390, 2014.
Marcus, M., et al. "Building a Large Annotated Corpus of English" The Penn Treebank, Oct. 1993. http://repository.upenn.edu/cis_reports.
McDonald, R., et al. "Universal Dependency Annotation for Multilingual Parsing", Proceedings of the 51st Annual Meeting of the Association for Computational Linguistics, pp. 92-97, Sofia, Bulgaria, Aug. 4-9, 2013.

Nagata, R., "Language Family Relationship Preserved in Non-Native English", Proceedings of COLING, 2014, 25th International Conference on Computational Linguistics, pp. 1940-1949, Dublin, Ireland, Aug. 23-29, 2014.
Nagata, R., et al., "Reconstructing an Indo-European Family Tree from Non-native English Texts", Proceedings fo rhte 51st Annual Meeting of the Association of Computational Linguistics, pp. 1137-1147, Sofia, Bulgaria, Aug. 4-9, 2013.
Oldin, T., et al. "JALT Journal: Journal of the Japan Association of Language Teachers" Cambridge University, 11(2), Dec. 1989.
Petrov, S., "A Universal Part-of-Speech Tagset", LRCE, 2012.
Roberts, L., "Using Eye-Tracking to Investigate Topics in L2 Acquisition and L2 Processing", Studies in Second Language Acquisition (35(02):213-215, 2013.
Swanson, B., et al. "Data Driven Language Transfer Hypotheses", Proceedings of the 14th Conference of the European Chapter of the Association for Computational Linguistics, pp. 169-173, Gothenburg, Sweden, Apr. 26-30, 2014.
Swanson, B., et al., "Extracting the Native Language Signal", Proceedings of NAACL-HLT 2013, pp. 85-94, Atlanta, Georgia, Jun. 9-14, 2013.
Tetreault, J., et al. "A Report on the First Native Language Identification Shared Task", Proceedings of the Eighth Workshop on Innovative Use of NLP for Building Educational Applications, pp. 48-57, Atlanta, Georgia, Jun. 13, 2013.
Tsur, O., et al. "Using Classifier Features for Studying the Effect of Native Language on the Choice of Written Second Language Words", Proceedings of the Workshop on Cognitive Aspects of Computational Language Acquisition, pp. 9-16, Prague, Czech Republic, Jun. 2007.
Ward, J.H, "Hierarchical Grouping to Optimize an Objective Function", Journal of the American Statistical Association, vol. 58, No. 301 (Mar. 1963), pp. 236-244.
Yannakoudakis, H., et al. "A New Dataset and Method for Automatically Grading ESOL Texts", Proceedings of the 49th Annual Meeting of the Association for Computational Linguistics, pp. 180-189, Portland, Oregon, Jun. 19-24, 2011.
Martohardjono, G., et al. "Language transfer: what do we really mean", In L. Eubank, L. Selinker, and M. Sharwood Smith, editors, The current state of Interlanguage: studies in honor of William E. Rutherford, John Benjamins:The Netherlands, pp. 205-219, 1995.
Rosa, A., "Crosslinguistic Influence in Second Language Acquisition" vol. 95, Multilingual Matters. 2015.
Berkes, E, "Multilingual: New perspectives on syntactic development", The Handbook of Bilingualism and Multilingualism, Second Edition pp. 137-167, 2012.
Hammarstrom, H., "Max Planck Institute for Evolutionary Anthropology", Leipzig. Jan. 1, 2015 https://web.archive.org/web/20150101011442/https://glottolog.org/—downloaded from Internet Feb. 8, 2019.
Jarvis, S., et al. "Approaching Language Transfer Through Text Classification Explorations in the Detection-based Approach" vol. 64, Multilingual Matters. 2012.
Dryer, M.S., et al. "Max Planck Institute for Evolutionary Anthropology", WALS online. Leipzig., Jan. 2, 2013, https://web.archive.org/web/20130102094508/http:/wals.info/ downloaded Feb. 8, 2019.
Piantadosi, S.T., et al., "Word Lengths are Optimized for Efficient Communication", Proceedings for the National Academy of Sciences, 108(9): 3526-3529. Dec. 2010.
Santorini, B., Part-of-Speech Tagging Guidelines for the Penn Treebank Project (3rd Revision), Technical Reports, (CIS) 1990.
Tetreault, J., et al. "Native Tongues, Lost and Found: Resources and Empirical Evaluations in Native Language Identification", Technical Papers, pp. 2585-2602, COLING, 2012.
Littel, P., et al. URIEL Typological Database. Pittsburgh:Carnegie Mellon University. http://www.cs.cmu.edu/ dmortens/uriel.html—downloaded from Internet Feb. 7, 2019.
Notice of Allowance for U.S. Appl. No. 16/130,627 dated Jan. 21, 2021 titled "Eye Tracking As a Language Proficiency Test".
PTO Response to Rule 312 Communication for U.S. Appl. No. 16/130,627 dated Feb. 19, 2021 titled "Eye Tracking As a Language Proficiency Test ".

Fig. 1 100

|        | Word 1 | Word 2 | Word 3 | Word 4 | Word 5 | Word 6 | Word 7 | Word 8 | Word 9 |
|--------|--------|--------|--------|--------|--------|--------|--------|--------|--------|
| Word 1 |        |        |        |        |        |        |        |        |        |
| Word 2 |        | 1      |        |        |        |        |        |        |        |
| Word 3 |        |        | 2      |        |        |        |        |        |        |
| Word 4 |        |        |        | 3      |        |        |        |        |        |
| Word 5 |        |        | 1      |        | 2      |        |        |        |        |
| Word 6 |        |        |        |        |        | 1      |        |        |        |
| Word 7 |        |        |        |        |        |        | 2      |        |        |
| Word 8 |        |        |        |        |        | 2      |        | 3      |        |
| Word 9 |        |        |        |        |        |        |        |        | 4      |

PREDICTING NATIVE LANGUAGE FROM GAZE

RELATED APPLICATIONS

This application claims the benefit of U.S. Provisional Application No. 62/558,710, filed on Sep. 14, 2017 and U.S. Provisional Application No. 62/558,765 filed on Sep. 14, 2017. This application is also related to U.S. application Ser. No. 16/130,627, filed Sep. 13, 2018. The entire teachings of the above applications are incorporated herein by reference.

GOVERNMENT SUPPORT

This invention was made with Government support under Grant No. CCF-1231216 awarded by the National Science Foundation. The Government has certain rights in the invention.

BACKGROUND

Currently, determining a person's native language is done using a written sample from that person. Such tests can be judged solely based on the person's written sample.

SUMMARY

Currently, however, eye gaze or eye tracker technology has not been used to predict native language of a target user (e.g., the person participating and having eye movements tracked).

In an embodiment, a method of Applicant's disclosure predicts native language by having users read sentences. Applicant's method records gaze location during sentence reading with an eye tracker camera that returns raw eye gaze data or fixations and saccades of the user. In one embodiment, users read randomly sampled sentences (e.g., from a newspaper such as the Wall Street Journal (WSJ) or New York Times (NYT), etc.). Using the gaze recording, embodiments extract a set of linguistically motivated features that robustly characterize the gaze patterns of the reader. A processor employs these features in a supervised machine learning method (e.g., using a neural network classifier), which predicts the native language of the user. Feature extraction and prediction are fast, taking a few seconds at most. In an embodiment, the classifier is a logistic regression classifier, but a person having ordinary skill in the art can recognize that other classifiers and neural network classifiers can be employed.

Applicants tested the system embodiment extensively on native speakers of many languages including Chinese, Japanese, Spanish, Portuguese, and English. The method can distinguish reliably, with over 90% accuracy, between substantially different languages like Japanese and Spanish. The method can distinguish, with above chance accuracy, between more similar language pairs. Furthermore, the system can distinguish between native and non-native speakers, irrespective of their reading speed. The system is effective both when users and training readers read the same set of sentences ("Fixed Text embodiment") and when they read any set of sentences ("Any Text embodiment"). In certain embodiments, however, the sentences can be loaded from any source or be designed specifically for Applicant's method.

In an embodiment, a method includes presenting, on a display, sample text in a given language to a user. The method further includes recording eye fixation times for each word of the sample text for the user and recording saccade times between each pair of fixations of the sample text. The method further includes comparing features of the gaze pattern of the user to a gaze pattern of a plurality of training readers of text of the given language. Each reader (e.g., training user, training reader) has a known native language. The method further generates an estimate of a native language of the user based on the results of the comparison.

In an embodiment, the output can be a most likely estimated language, one or more estimated languages and their respective probabilities, or a probabilistic distribution of estimated languages.

In an embodiment, generating the estimate of the native language further includes generating a confidence score or probability of one or more languages being the native language of the user. For example, certain classifiers can provide a prediction or estimate of a native language without a probability, and other classifiers can provide a probability of one or multiple languages being a native language.

In an embodiment, generating the estimate of the native language of the user further includes generating predicted linguistic properties of a native language of a user. An example of a linguistic property can be presence of certain parts of speech (e.g., determiners) or word order.

In an embodiment, the method generates the features representing the gaze pattern of the user further by determining speed normalized features for words of the sample text.

In an embodiment, the method generating the features representing the gaze pattern of the user by determining speed normalized feature averages for clusters of words of the sample text, the clusters based on one or more of part of speech labels, syntactic relation labels, information content, word identity, word frequency, word surprisal, and word length based on the recorded eye fixation times and saccade times. The features can include one or more of first fixation duration (FF), first pass duration (FP), total fixation duration (TF), regression path duration (RP), and word skips (WS).

In an embodiment, the method may include generating the features representing the gaze pattern of the user by, for a sentence of the sample text, determining a scan path representing a temporal sequence of fixations and saccades for the sample text. Determining the scan path for the sentence further includes generating a transition table having a number of rows and number of columns equal to the number of words in the sentence. A first dimension of the table represents a first word beginning a saccade and the second dimension of the table represents a second word ending a saccade. Each entry in the table represents a number or fraction of the saccades from the first word to the second word.

A person having ordinary skill in the art can recognize that the eye tracking record can be pre-processed in other ways than described herein, and transformed into other feature sets or other representations than the ones described herein. Such representations can divide the gaze trajectory into saccades and fixations, or use any other division of the eye tracking record into time periods, including using the location of the user's gaze at each individual sample time. The features can include any combination of the feature sets described herein, as well as any combination of other features, or a combination of both.

In an embodiment, the fixations and saccades can be based on fixation and movement between: words, word sequences, and other word groupings based on the syntactic or semantic structure of the sentence.

In an embodiment, a model can be generated by tracking and analyzing multiple training readers read text in a given language, where the multiple training readers have a number of different known native languages. That model can then be used to present text in a given language to a user being tested to determine an estimated native language among the different native languages of the training readers, or to determine linguistic properties of the user's native language, which can be converted to an estimated native language. However, a person having ordinary skill in the art can recognize that additional models can be generated by tracking and analyzing multiple training readers read text in a second language, so that a user can be presented with text in the second language to determine an estimated native language among the different native languages of the training readers, or to determine linguistic properties of the user's native language, which can be converted to an estimated native language.

In an embodiment, a device for predicting native language, includes an eye tracker recording gaze location of a user reading sample text shown by display monitor in a given language. The device can include a processor coupled to eye fixation times for each word of the sample text for the user and recording saccade times between each pair of fixations. The processor can be further configured to compare features of the gaze pattern of the user to a gaze pattern of a plurality of readers of text of the given language. Each reader has a known native language. The processor is further configured to generate an estimate of a native language of the user based on the results of the comparison.

In an embodiment, a non-transitory computer-readable medium configured to store instructions for determining language proficiency of a user. The instructions, when loaded and executed by a processor, cause the processor to present, on a display, sample text in a given language to a user. The instructions further cause the processor to record eye fixation times for each word of the sample text for the user and record saccade times between each pair of fixations. The instructions further cause the processor to compare features of the gaze pattern of the user to a gaze pattern of a plurality of readers of text of the given language. Each reader has a known native language. The processor is further configured to generate an estimate of a native language of the user based on the results of the comparison.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

The teachings of all patents, published applications and references cited herein are incorporated by reference in their entirety.

Figure 1:
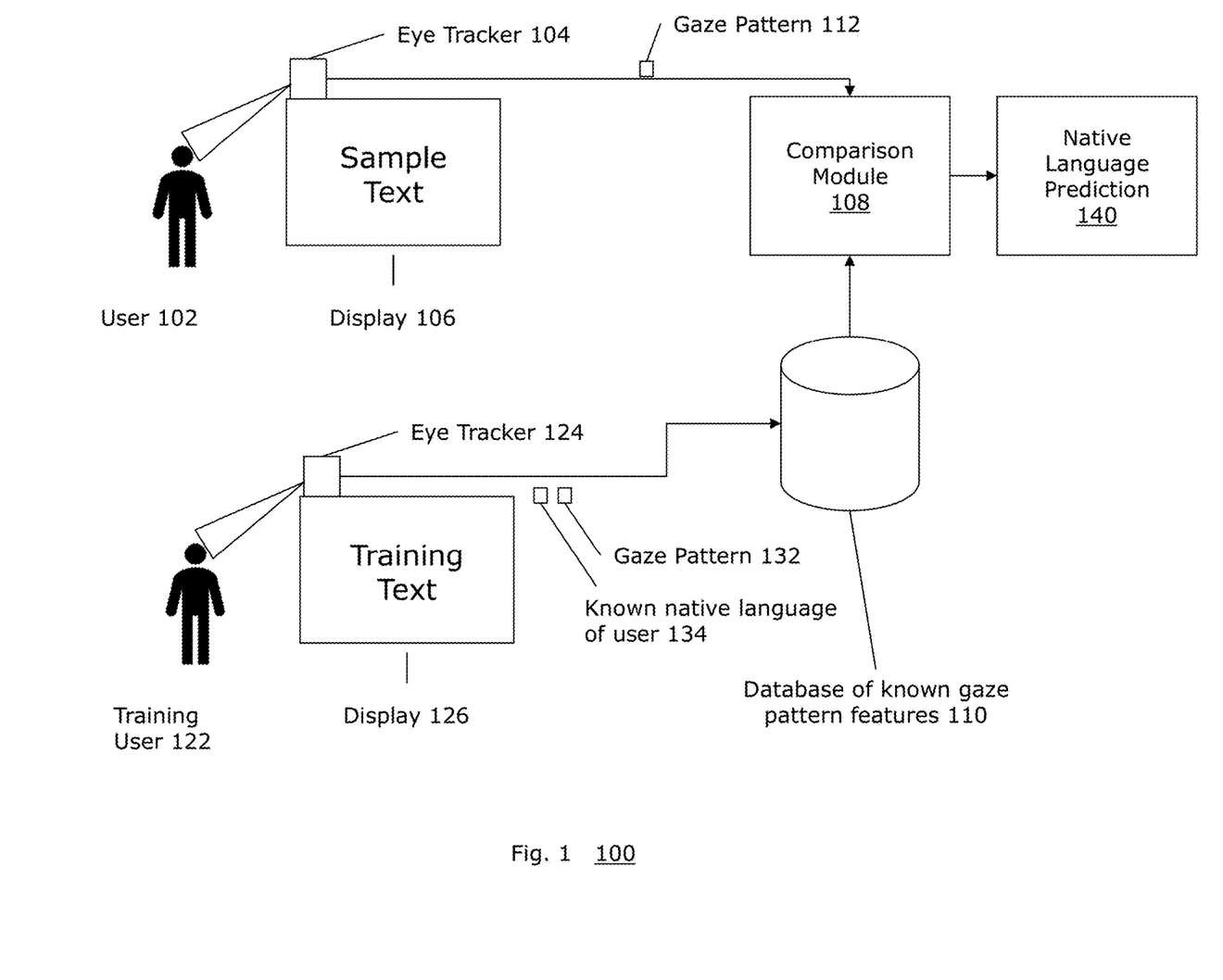
FIG. 1 is a block diagram illustrating an example embodiment of the present technology.

FIG. 1 is a block diagram 100 illustrating an example embodiment of the present technology. First, training user(s) 122 (e.g., reader, training reader) read a training text on a display 126 while an eye tracker 124 captures images of the training user's 122 eyes. The eye tracker 124 captures the movement of the training user's 122 eyes relative to the display 126, and can capture the focus of a training user's 122 gaze for each period of time. In one embodiment, the eye tracker 124 captures the focus of the training user's 122 gaze at each millisecond (e.g., 1,000 Hz). The data the eye tracker 124 outputs is referred to in FIG. 1 as a gaze pattern 132. The gaze pattern 132 can include the raw images of the user's eye, or data relating to fixations and saccades of the training user's 122 text. The fixation and saccade data can indicate which words or spaces the training user's 122 eye is focused on in a given frame, or be even more granular and indicate which character or letter the training user's 122 eye is focused on.

The system uses gaze pattern 132 to train a classifier (e.g., a neural network) using each training user 122 (e.g., training reader). Each gaze pattern 132 is associated with a known native language of the training user (e.g., English, Spanish, Chinese, etc.). The system trains the classifier (e.g., database 110) based on the gaze pattern 132 and the known native language 134 of the training user 122 (e.g., training reader) in the language.

After the model is trained, the system can predict a user's 102 native language. A display 106 displays a sample text to the user. While the user 102 reads the sample text, an eye tracker 104 tracks the user's eyes. In one embodiment, the sample text can be a same text as the training text, but in another embodiment can be a different text. Both embodiments are described below in further detail. Like eye tracker 124, the eye tracker 104 captures movements of the user's 102 eyes relative to the display 106, and can capture the focus of a user's eye for each period of time. The features of the eye tracker 104 and 124 can be interchangeable, and in embodiments can be the same eye tracker.

The eye tracker 104 outputs a gaze pattern 112 of the user 102. A comparison module 108 compares the gaze pattern of the user 102 reading the sample text to users 122 reading the sample text using classifier (e.g., neural network) trained on the features extracted from the training users 122 reading training texts. Based on the comparison, the system outputs a native language prediction/predicted native language 140.

Applicant's native language prediction 140 can be useful for forensic, advertisement/marketing-related, and educational applications. The embodiments of a system and method presented herein can be used from any location using existing mobile eye trackers. As laptop and mobile phone cameras improve, Applicant's system and method can be deployed on such devices as well.

Figure 2:
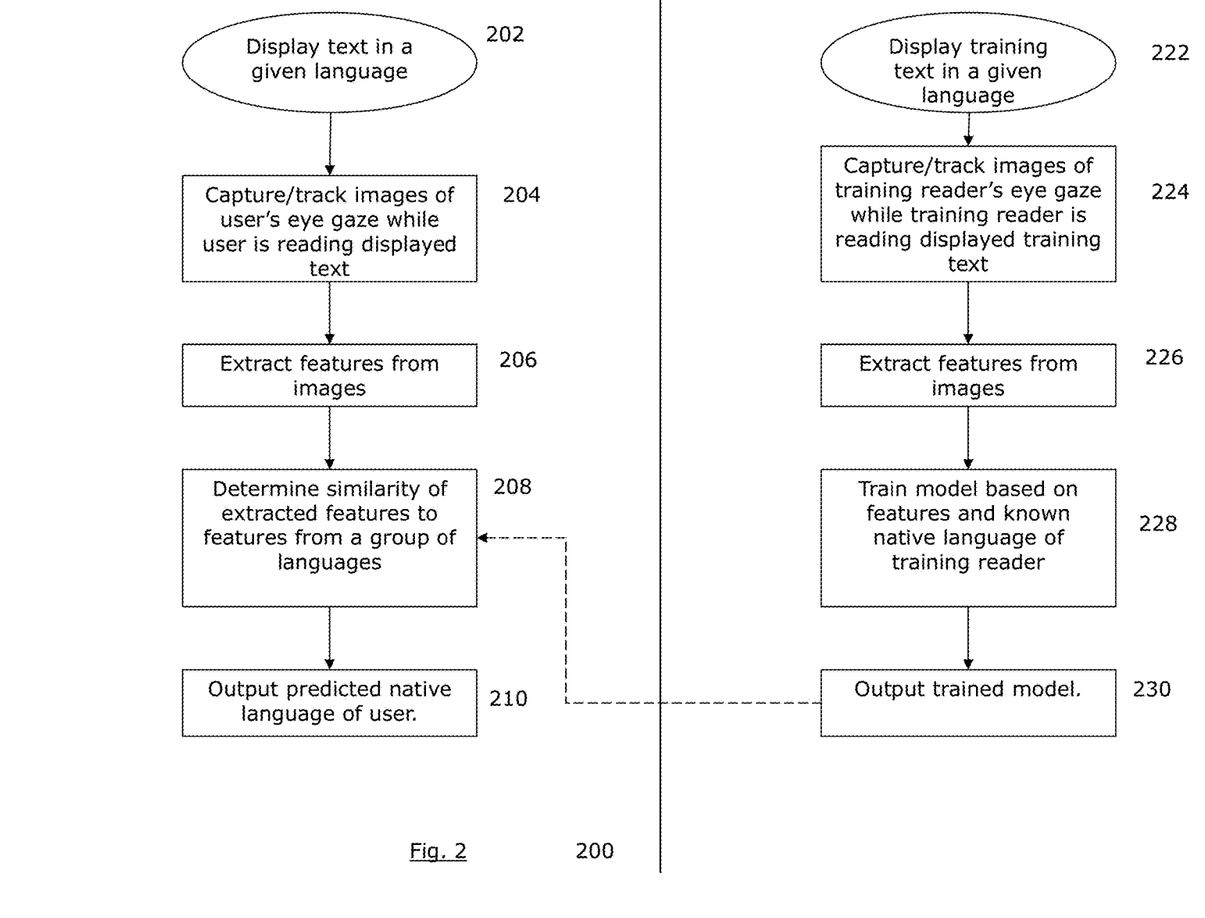
FIG. 2 is a flow diagram illustrating an example embodiment of the present technology.

FIG. 2 is a flow diagram 200 illustrating an example embodiment of the present technology. FIG. 2 illustrates two methods in parallel: a testing method (202-210) and a training method (222-230), however, these methods are linked and can be performed in parallel. For example, training can continue to add data the trained model while testing is underway. However, to aide in the description of both methods, training is described first below.

In training, text is displayed to a user in a given language (222). The method captures/tracks images of a user's eye gaze while the user is reading displayed training text (224). The method extracts features from the images (226). These features can be low-level features, based on or derived from saccades and fixations, or higher level linguistic features, as described in further detail below. From the features, the method trains the model based on features and a known native language of the training user (228), and outputs that trained model (230).

In testing a user, the method displays text in a given language to a user (202). The method then captures/tracks images of the user's gaze while user is reading displayed text (204). The method extracts features from the images (206). These features can be low-level features, based on or derived from saccades and fixations, or higher level linguistic features, as described in further detail below. The method compares the extracted features from the testing user to the extracted features of the training user using the outputted trained model 230 (208). Then, based on the comparison, the method outputs a known native language of the testing user (210).

To predict native language, users read a small set of free-form sentences. The user's gaze location is recorded during sentence reading with an eye tracker/eye tracking camera. The free-form sentences consist of 78 sentences. Each sentence appears on a blank screen as a one liner. However, the text can appear as a full paragraph, page, or in other increments. Upon completion of sentence reading, users and training readers answer a comprehension question (e.g., binary question, multiple choice question, or other comprehension question) regarding whether the user and training reader understood the sentence. The questions are introduced to encourage attentive reading and to obtain a complementary measure of reading comprehension. Both the sentences and the questions are triggered by a short gaze of 300 ms on a fixation target which appears on a blank screen and is co-located with the beginning of the text in the following screen. Users and training readers use a controller to input reading completion and to answer the comprehension questions. However, this is one embodiment of a setup for Applicant's system and method that can be modified in various ways, including embodiments having presentation of multiple sentences at a time and omission of fixation targets and reading comprehension questions.

The reading material consists of free-form English or target language sentences. There is no restriction on the form and content of the sentences, and they can be obtained from any textual source. One embodiment uses randomly selected newswire sentences. A database includes annotations of sentences having linguistic information, including part-of-speech tags and syntactic trees, however, these annotations are not displayed to the user.

Using the gaze recording, an embodiment extracts a set of linguistically motivated features which robustly characterize the gaze patterns of the reader. These features are then used in a supervised machine learning process (e.g., classifier), which predicts the native language of the user. Feature extraction and prediction are very fast, taking a few seconds at most.

Eye movement during reading is closely related to linguistic characteristics of the text and reflects ways in which readers engage with the text. Applicant's system and method leverages these principles to introduce a novel, cognitively driven technology for recording and analyzing eye-tracking records and using them to determine native language.

Applicant's approach includes two components. The first component is a collection of gaze feature sets which robustly summarize eye movement during reading. The feature sets provide linguistically motivated characterizations of gaze trajectories which enable highly informative comparisons of reading patterns across different readers, and crucially, across different sentences. The second component comprises mechanisms for prediction of native language via matching of gaze features of a testing user and native language speaking users (e.g., training users) using a neural network.

Eye tracking devices record the location of the reader's gaze over time (the sampling rate of one embodiment eye tracker is 1000 Hz). Embodiments transform this recording into several feature sets that summarize the reading patterns of the reader. The features are linguistically motivated and designed to be robust to uninformative variation stemming from personal reading styles.

The features are based on an established division of the gaze trajectory to fixations (e.g., stops) and saccades (e.g., movements between fixations). In particular, several feature sets use one or more or a combination of any of the following reading metrics, however, other reading metrics can be used:

a) First Fixation Duration (FF)—duration of the first fixation on a word.
b) First Pass Duration (FP)—time spent from gaze first entering a word to gaze first leaving it, which includes re-fixations within the word.
c) Total Fixation Duration (TF)—the sum of all fixation times on a word.
d) Regression Path Duration (RP)—the time from first entering a word until proceeding to its right.
e) Word Skips—whether a word was skipped or not.
f) Saccade Length—the distance between two fixations
g) Landing location within a word—the location (e.g., on a normalized 0-1 scale) of the first fixation on a word.
h) Saccade direction—the direction (e.g., forward or backwards) of the saccade.
i) Number of fixations—the total number of fixations.
j) Number of regressions—the number of saccades with a backwards saccade direction.

Another feature set are word property coefficients, which measure the extent to which linguistic properties of words, such as word length, word frequency, and word surprisal, influence reading times (FF, FP, TF, RP, and word skips).

Bigram, and trigram sequences are referred to as $seq_{i,k} = w_i, \ldots, w_{i+k-1}$, $k \in \{1,2,3\}$, where for each metric $M \in \{FF, FP, TF, RP\}$ the fixation time for a sequence $m_{seq_{i,k}}$ is defined as the sum of fixations on individual tokens $M_w$ in the sequence.

$$M_{seq_i,k} = \Sigma_{w' \in seq_{i,k}} M_{w'} \qquad (1)$$

A person having ordinary skill in the art can recognize that the sequences can be expanded to higher order ngrams or other groupings of words based on syntactic or semantic criteria.

Another aspect of the native language identification method is that it controls for (e.g. normalizes) the reading speed of the reader. The above listed fixation duration measures are normalized for each word as follows to minimize the variable of reading speed of the reader. First, Applicant's method defines a normalization constant as a metric's fixation time per word in the word's context. For feature sets applicable only to the Fixed Text embodiment, the context is defined as the sentence in which the word appears. For features applicable to both the Fixed Text and Any Text embodiments, the context is the entire textual input presented to the reader. Applicant's method then obtains a normalized fixation duration metric by dividing the word's fixation metric by this term.

Therefore, for each metric M and sequence $seq_{i,k}$, the method normalizes the sequence fixation time $M_{seq_{i,k}}$ relative to the subject's sequence fixations times in the textual context of the sequence. The context C is defined as the sentence in which the sequence appears for the Words in Fixed Context feature-set and the entire textual input for the linguistic clusters feature-sets, as described below. The normalization term $S_{M,C,k}$ is defined as the metric's fixation time per sequence of length k in the context:

$$S_{M,C,k} = \frac{1}{|C|} \sum_{seq_k \in C} M_{seq_k} \quad (2)$$

The method can then obtain a normalized fixation time $$M_{norm_{seq_{i,k}}}$$

as:

$$M_{norm_{seq_{i,k}}} = \frac{M_{seq_{i,k}}}{S_{M,C,k}} \quad (3)$$

The Fixed Text embodiment includes the following feature sets.

Words in Fixed Context: This feature set includes a speed normalized FF, FP and TF for individual words appearing in a fixed context across readers. This is a token-based feature set, which requires the same textual input for all users and testing readers, and is thus applicable only in the Fixed Text regime.

Scan Path: This feature set includes an N×N transition table M between words, for a sample having N words. Each entry of the Table M, M(i,j), indicates the number of saccades from word i to word j. These counts are normalized by the total number of saccades recorded during sentences reading. Similar to Words in Fixed Context, this feature set is applicable only when gaze data from multiple subjects is available for the same given sentence that the testing user reads.

Figure 3:
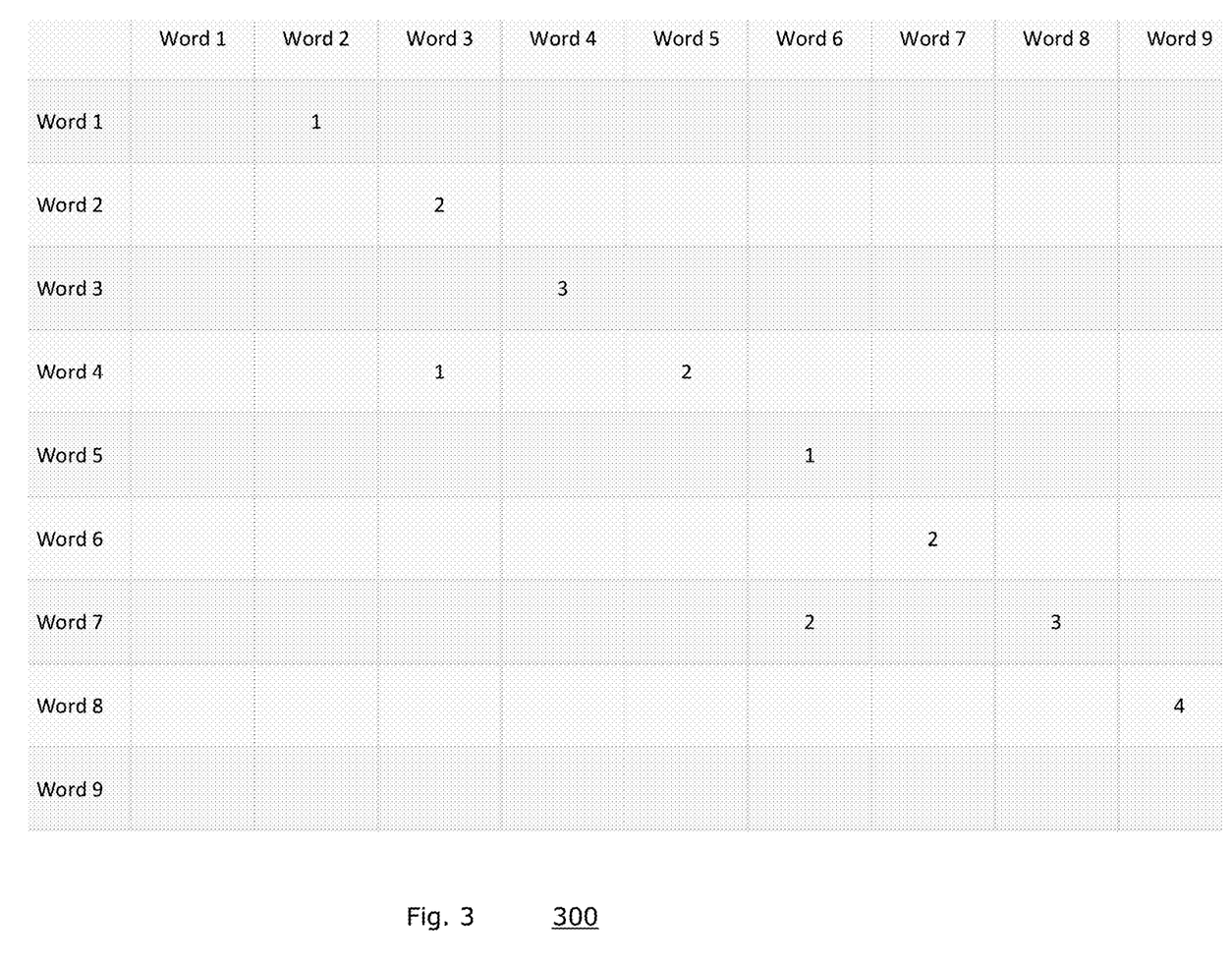
FIG. 3 illustrates an example embodiment of a scan path table having nine words.

FIG. 3 illustrates an example embodiment of a scan path table having nine words (e.g., N=9). Each number can represent a number of saccades from one word to the next. For example, from Word 1 to Word 2, there is 1 saccade unit indicated by the table of FIG. 3. A person having ordinary skill in the art can recognize that saccades are listed from each word to the next word. However, saccades can also be recorded for words read out of order. For example, the table indicates a saccade is recorded for the reader moving its gaze from word 4 backwards to word 3 for 1 saccade units, and word 7 backwards to word 6 for two saccade units.

The Any Text embodiment includes the following feature sets. However, the fixed set embodiment can also include these feature sets.

Reading Time Coefficients: The reading time coefficients of regression models that predict word reading times (FF, FP, TF, Word Skipping and RP) from word characteristics such as length, frequency, and surprisal (currently implemented as trigram probability).

Saccade Length: Average saccade length

Landing Site: average first fixation position within a word (normalized, e.g., on a scale of 0 to 1).

Linguistic Clusters: Average speed normalized FF, FP and TF for words clustered by part-of-speech tags, syntactic relation labels and information content (e.g., a metric that can be approximated using word length). As described below, this abstraction over gaze trajectories is effective both in the Any Text and the Fixed Text embodiments. The respective feature set can be extended to include additional linguistic clustering criteria.

Each feature set is pre-processed for each individual feature by deriving a zero mean unit variance scaler from the training set feature values, and applying the scaler to transform both the training and test values of the feature to Z scores.

In one embodiment, the method employs individual words as units of analysis. In another embodiment, the method computes fixation based features for word sequences (ngrams or n-grams) and other word groupings (e.g. based on the syntactic or semantic structure of the sentence).

In an embodiment, Applicant builds the following log-linear model:

$$p(y | x; \theta) = \frac{\exp(\theta \cdot f(x, y))}{\sum_{y' \in Y} \exp(\theta \cdot f(x, y))} \quad (4)$$

Where y is the reader's native language, x is the reading input and θ are model parameters. The model is trained with gradient descent using limited memory Broyden-Fletcher-Goldfarb-Shanno (L-BFGS).

Textual patterns in a given language are linked with linguistic similarities of respective native languages. In particular, native language identification (NLI) classification uncertainty correlates with similarities between languages with respect to their typological features. Applicant's method herein shows that this also applies to NLI from reading (NLIR) using features from gaze/eye tracking. This can be used to obtain linguistic information about the native languages directly from reading patterns in a given (non-native) language.

Classification uncertainty for a pair of languages y and y' in a data collection D is defined as the average probability assigned by the NLIR classifier to one language given the other being the true native language. Doing so does not rely on the actual performance of the classifier, but instead interprets classifier uncertainty as a similarity measure between the respective languages and denotes it as a Given Language Reading Similarity (GLRS) as in Equation 5 below:

$$GLRS_{y,y'} = \frac{\sum_{(x,y) \in D_y} p(y' | x; \theta) + \sum_{(x,y) \in D_{y'}} p(y | x; \theta)}{|D_y| + |D_{y'}|} \quad (5)$$

Instead of classifier uncertainty, the method can compare gaze feature similarity of users having different native languages using a measure like Cosine. Applicant's method compares these reading similarities to the linguistic similarities between native languages and shows a strong correlation between the two. To approximate linguistic similarities, features are extracted from the gaze/eye tracking data of the user (e.g., by URIEL's lang2vec tool). The features aggregate, fuse, and normalize typological, phylogenetic, and geographical information about different languages. As one example, 103 morphosyntactic features are available in URIEL, which are derived from the World Atlas of Language Structures (WALS, by Drayer and Haspelmath 2013), Syntactic Structures of the World's Languages (SSWL, by Collins and Kayne, 2009) and Ethnologue (by Lewis et al., 2015), the contents of which are incorporated by reference in their entirety. Applicant's method further employs URIEL's 3,718 language family features, each feature representing membership in a branch of Glottolog's world language tree. Truncating features with the same value for all our languages leaves 76 features having 49 syntactic features and 27 family tree features. The linguistic similarity LS between a pair of languages y and y' is then determined by the cosine similarity of their URIEL feature vectors:

$$LS_{y,y'} = \frac{v_y v_{y'}}{\|v_y\| \|v_{y'}\|} \quad (6)$$

Applicant's method can not only predict or classify a user's native language and establish global linguistic similarity between native languages, but can identify specific reading patterns that are characteristic of different native languages. Applicant's system can further determine relations of observed reading time differences to grammatical errors committed by speakers of different native languages and to specific linguistic properties of the native language. For example, Chinese and Japanese native speakers when reading certain languages, such as English, tend to have shorter reading times for determiners (e.g., articles) because their native language does not have an equivalent of determiners. Native speakers of these language also have high rates of determiner omission errors in the given language. Such an observation can also be useful in predicting a native language; a speaker that skips over determiners may be more likely to have a native language that lacks determiners. The same may apply for other parts of speech and other languages.

Based on the above, the system can further generate a prediction of one or more linguistic properties of a native language of the testing user. For example, the system can generate a probability or a list of whether the native language has determiners, the word order of the language, etc. From that, the system can determine, based on information in a linguistic database (e.g., WALS) a most likely language based on the predicted list of linguistic properties. In this embodiment, the system can predict native languages without having a training reader/training user having that particular native language.

Applicants tested an embodiment system extensively on native speakers of Chinese, Japanese, Spanish and Portuguese as well as native speakers of English, obtaining strong results despite limited training data. The system is effective with both the Fixed Text and Any Text embodiments, however, the Fixed Text embodiment can show more accurate results in some cases.

Embodiments can distinguish reliably, with over 90% accuracy, between substantially different languages like Japanese and Spanish. An embodiment can also tell apart with above chance accuracy more similar language pairs. Furthermore, the embodiments can distinguish between native and non-native speakers, irrespective of their reading speed.

Setup of embodiments can be straightforwardly extended to additional non-native languages by collecting training data for those languages. Moreover, one embodiment uses English, but the same technology can be applied to text in other languages for other embodiments.

Applicant's embodiment can be applied to non-native languages and reading in languages other than English. The performance of the system can increase further as more training data is collected.

Figure 4:
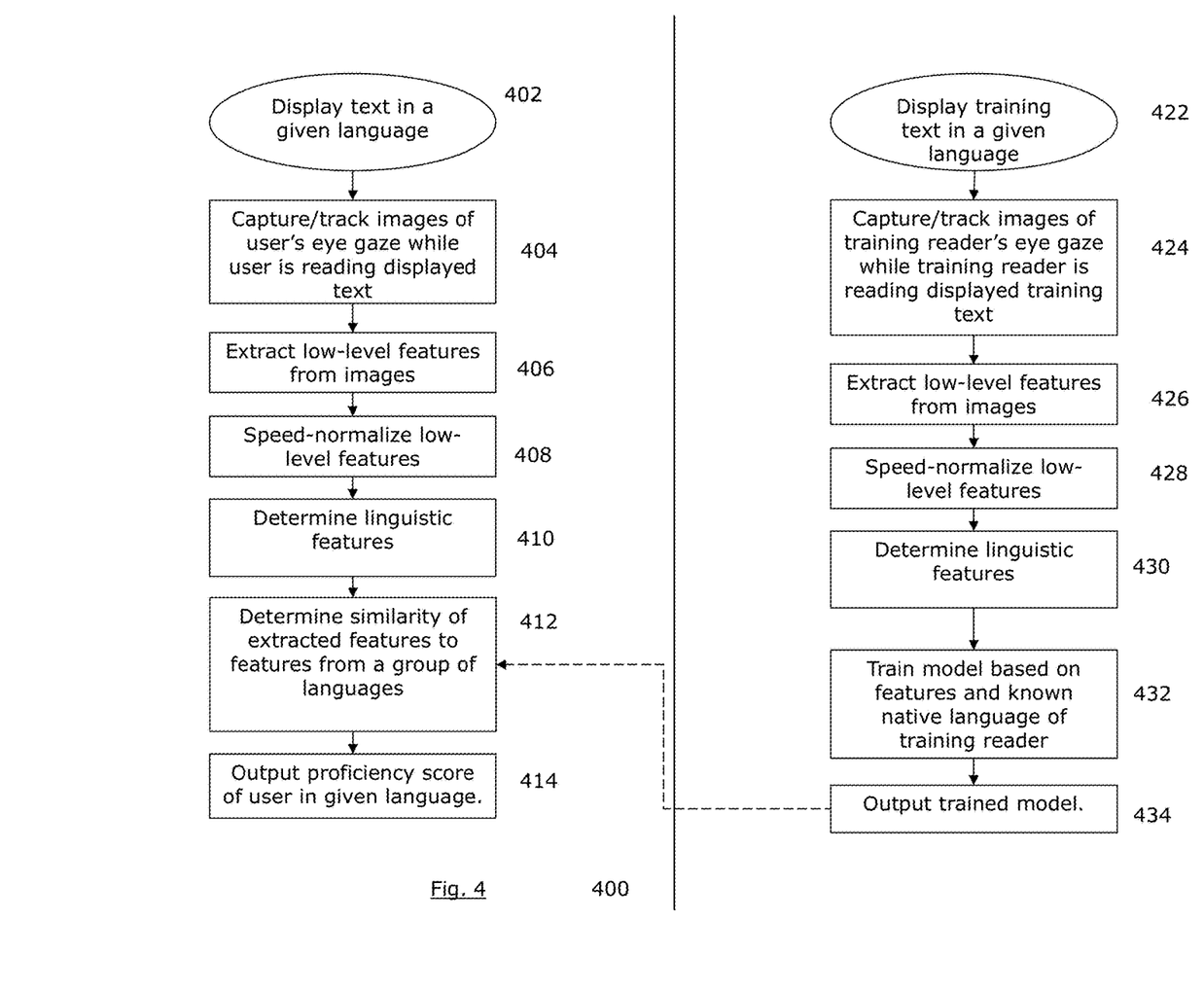
FIG. 4 is a flow diagram illustrating a method employed by an embodiment of the present invention.

FIG. 4 is a flow diagram 400 illustrating a method employed by an embodiment of the present invention. FIG. 4 illustrates two methods in parallel: a testing method (402-414) and a training method (422-434), however, these methods are linked and can be performed in parallel. For example, training can continue to add data the trained model while testing is underway. However, to aide in the description of both methods, training is described first below.

In training, text is displayed to a user in a given language (422). The method captures/tracks images of a user's eye gaze while the user is reading displayed training text (424). The method extras low-level features from the images, where low-level features are fixations and saccades (e.g., eye movements of the user) (426). The method then speed-normalizes the low-level features (428), as described in relation to Equations 1-3 above. From the speed normalized features, the method calculates higher level linguistic cluster features (430). From the features, the method trains the model based on features and a known native language of the training user (432), and outputs that trained model (434).

In testing a user, the method displays text in a given language to a user (402). The method then captures/tracks images of the user's gaze while user is reading displayed text (404). The method extracts low-level features from the images (406). The method then speed-normalizes the low-level features (428), as described in relation to Equations 1-3 above. From the speed normalized features, the method calculates higher level linguistic cluster features (430). From these higher level features, the method determines a similarity of features with speakers having a known native language (412). For example, one comparison may be of saccade and fixation times for a given part of speech (e.g., nouns, verbs, determiners, prepositions, etc.). Then, based on the comparison, the method outputs a native language of the testing user (414).

Figure 5:
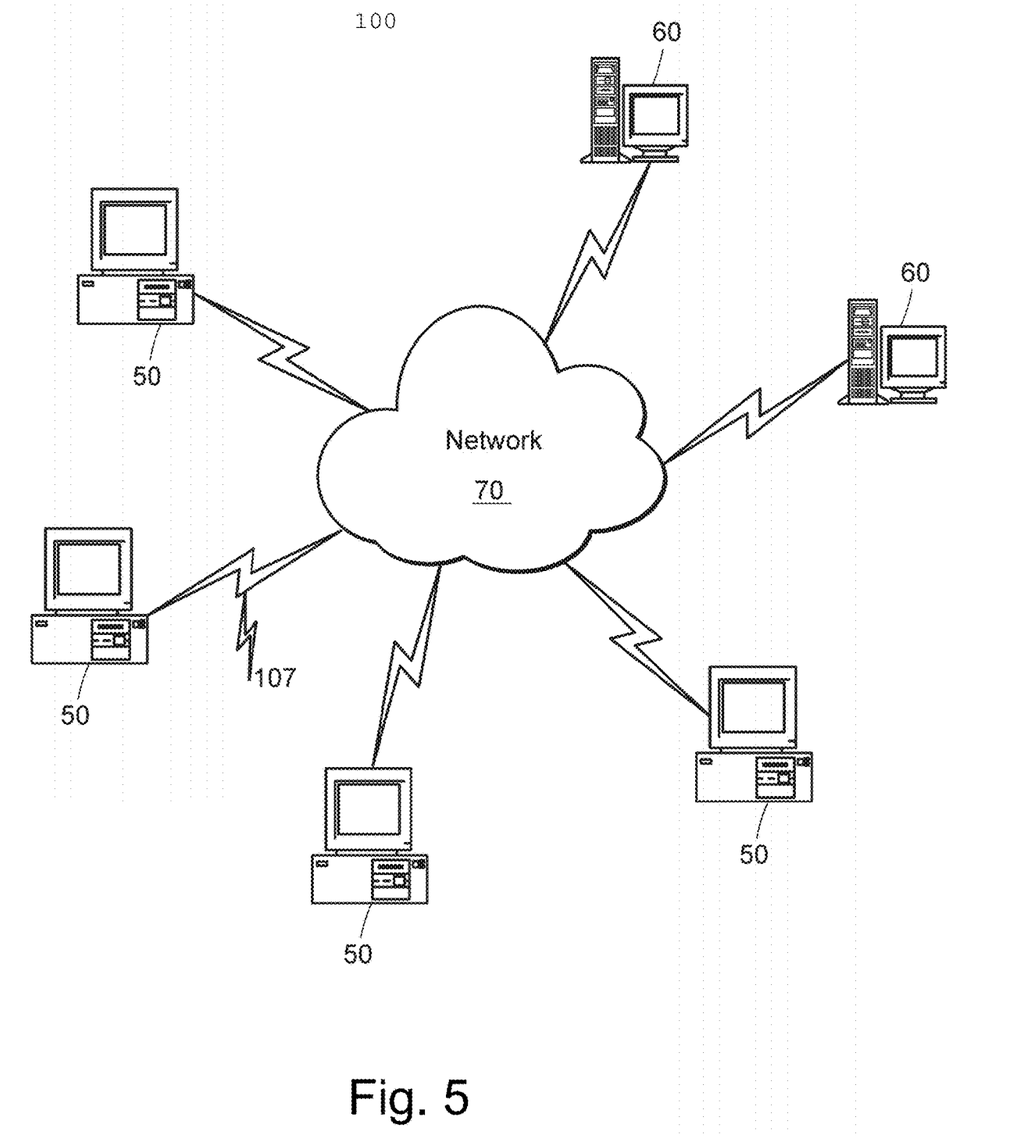
FIG. 5 illustrates a computer network or similar digital processing environment in which the present invention may be implemented.

FIG. 5 illustrates a computer network or similar digital processing environment in which the present invention may be implemented. Embodiments include systems 100, devices, (FIG. 1) methods (FIG. 2, 4), computer program products (FIG. 5, 6), and other implementations, and are generally referenced 100 in the Figures.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), cloud computing servers or service, a worldwide collection of computers, Local area or Wide area networks, and gateways that currently use respective protocols (TCP/IP, Bluetooth, etc.) to communicate with one another. Other electronic device/ computer network architectures are suitable.

Figure 6:
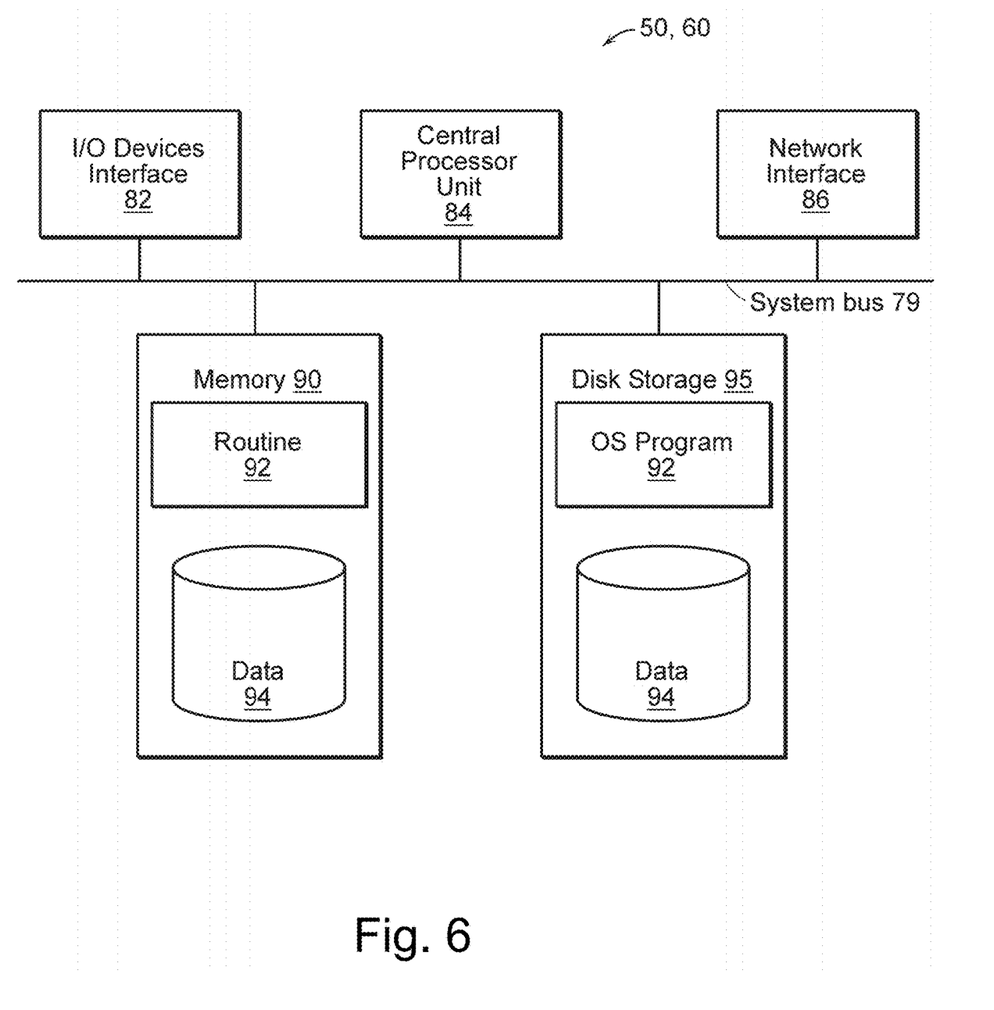
FIG. 6 is a diagram of the internal structure of a computer (e.g., client processor/device or server computers) in the computer system of FIG. 5.

FIG. 6 is a diagram of the internal structure of a computer (e.g., client processor/device 50 or server computers 60) in the computer system of FIG. 5. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 1). Memory 90 provides volatile storage for computer software instructions 92 and data 94 used to implement an embodiment of the present invention (e.g., code detailed above and in FIG. 3). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

In other embodiments, the program product 92 may be implemented as a so called Software as a Service (SaaS), or other installation or communication supporting end-users.

While example embodiments have been particularly shown and described, it will be understood by those skilled in the art that various changes in form and details may be made therein without departing from the scope of the embodiments encompassed by the appended claims.

What is claimed is:

1. A method comprising:
presenting, on a display, sample text in a given language to a user;
recording eye fixation times for each word of the sample text for the user;
recording saccade times between each pair of fixations;
comparing features of the gaze pattern of the user to features of a gaze pattern of a plurality of training readers of text of the given language, each training reader having a known native language; and
generating an estimate of a native language of the user based on the results of the comparison.

2. The method of claim 1, wherein generating the estimate of the native language further includes generating a confidence score or probability of one or more languages being the native language of the user.

3. The method of claim 1, wherein generating the estimate of the native language of the user further includes generating predicted linguistic properties of a native language of a user.

4. The method of claim 1, further comprising:
generating the features representing the gaze pattern of the user further by determining speed normalized features for words of the sample text.

5. The method of claim 1, further comprising:
generating the features representing the gaze pattern of the user by determining speed normalized feature averages for clusters of words of the sample text, the clusters based on one or more of part of speech labels, syntactic relation labels, information content, word identity, word frequency, word surprisal, and word length based on the recorded eye fixation times, and saccade times.

6. The method of claim 1, wherein the features include one or more of first fixation duration (FF), first pass duration (FP), total fixation duration (TF), regression path duration (RP), word skips, saccade length, and location within a word.

7. The method of claim 1, further comprising:
generating the features representing the gaze pattern of the user further by, for a sentence of the sample text, determining a scan path representing a temporal sequence of fixations and saccades for the sample text.

8. The method of claim 7, wherein determining the scan path for the sentence further includes generating a transition table having a number of rows and number of columns equal to the number of words in the sentence, where a first dimension of the table represents a first word beginning a saccade and the second dimension of the table represents a second word ending a saccade, and each entry in the table represents a number or fraction of the saccades from the first word to the second word.

9. The method of claim 1, wherein fixations and saccades can be based on fixation and movement between: words, word sequences, and other word groupings based on the syntactic or semantic structure of the sentence.

10. A device for predicting native language, the device comprising:
an eye tracker recording gaze location of a user reading sample text shown by display monitor in a given language;

a processor coupled to record eye fixation times for each word of the sample text for the user and record saccade times between each pair of fixations, the processor further configured to:
  compare features of the gaze pattern of the user to features of a gaze pattern of a plurality of training readers of text of the given language, each training reader having a known native language; and
  generate an estimate of a native language of the user based on the results of the comparison.

11. The device of claim 10, wherein generating the estimate of the native language further includes generating a confidence score or probability of one or more languages being the native language of the user.

12. The device of claim 10, wherein generating the estimate of the native language of the user further includes generating predicted linguistic properties of a native language of a user.

13. The device of claim 10, wherein the processor is further configured to generate the features representing the gaze pattern of the user further by determining speed normalized features for words of the sample text.

14. The device of claim 10, wherein the processor is further configured to:
  generate the features representing the gaze pattern of the user by determining speed normalized feature averages for clusters of words of the sample text, the clusters based on one or more of part of speech labels, syntactic relation labels, information content, word identity, word frequency, word surprisal, and word length based on the recorded eye fixation times, and saccade times.

15. The device of claim 10, wherein the features include one or more of first fixation duration (FF), first pass duration (FP), total fixation duration (TF), regression path duration (RP), word skips, saccade length, and location within a word.

16. The device of claim 10, wherein the processor is further configured to:
  generate the features representing the gaze pattern of the user further by, for a sentence of the sample text, determining a scan path representing a temporal sequence of fixations and saccades for the sample text.

17. The device of claim 16, wherein determining the scan path for the sentence further includes generating a transition table having a number of rows and number of columns equal to the number of words in the sentence, where a first dimension of the table represents a first word beginning a saccade and the second dimension of the table represents a second word ending a saccade, and each entry in the table represents a number or fraction of the saccades from the first word to the second word.

18. The device of claim 10, wherein fixations and saccades can be based on fixation and movement between: words, word sequences, and other word groupings based on the syntactic or semantic structure of the sentence.

19. A non-transitory computer-readable medium configured to store instructions for determining language proficiency of a user, the instructions, when loaded and executed by a processor, causes the processor to:
  present, on a display, sample text in a given language to a user;
  record eye fixation times for each word of the sample text for the user;
  record saccade times between each pair of fixations;
  compare features of the gaze pattern of the user to features of a gaze pattern of a plurality of training readers of text of the given language, each training reader having a known native language; and
  generate an estimate of a native language of the user based on the results of the comparison.

20. The non-transitory computer readable medium of claim 19, wherein generating the estimate of the native language further includes generating a confidence score or probability of one or more languages being the native language of the user.

* * * * *